United States Patent [19]

Haunold et al.

[11] 4,213,703
[45] Jul. 22, 1980

[54] PHOTOMETER WITH STATIONARY SAMPLE HOLDER AND ROTATABLE SHUTTER

[75] Inventors: Otto Haunold, Carlsbad; Malbone W. Greene, Vista, both of Calif.

[73] Assignee: Beckman Instruments, Inc., Fullerton, Calif.

[21] Appl. No.: 910,819

[22] Filed: May 30, 1978

[51] Int. Cl.² ............................................. G01N 21/01
[52] U.S. Cl. .............................. 356/244; 250/361 C; 356/311; 422/54
[58] Field of Search .............. 356/311, 244; 250/239, 250/328, 361 C; 422/52, 104

[56] References Cited

U.S. PATENT DOCUMENTS

| | | | |
|---|---|---|---|
| 3,227,885 | 1/1966 | Hirai et al. | 250/239 |
| 3,370,175 | 2/1968 | Jordon et al. | 23/232 R |
| 3,764,214 | 10/1973 | Heiss | 356/440 |
| 3,877,817 | 4/1975 | Ralston | 250/239 |
| 3,917,404 | 11/1975 | Heiss | 356/317 |
| 4,066,365 | 1/1978 | Staunton | 356/244 |
| 4,099,920 | 7/1978 | Heiss | 422/52 |

*Primary Examiner*—Vincent P. McGraw
*Attorney, Agent, or Firm*—R. J. Steinmeyer; John E. Vanderburgh; Robert S. Frieman

[57] ABSTRACT

A sample holder and shutter assembly for photometers is disclosed in which a stationary sample chamber body is mounted in close proximity to a photosensitive device. A light path is provided from the sample chamber to the photosensitive device and shutter means is provided for selectively interrupting and opening the light path between the photosensitive device and the sample chamber without moving the sample chamber. Heat exchange means including a heat pump and a heat reservoir are provided for maintaining a desired temperature in the sample chamber. The sample chamber body is thermally connected to said heat pump and is preferably thermally isolated from the means mounting it. In one embodiment, the heat pump and heat reservoir are flexibly connected.

10 Claims, 6 Drawing Figures

PHOTOMETER WITH STATIONARY SAMPLE HOLDER AND ROTATABLE SHUTTER

FIELD OF THE INVENTION

This invention relates to photometers and more particularly to apparatus for detecting and measuring luminescence in materials.

BACKGROUND

The measurement of light absorbed by or emitted from a sample can provide a useful measurement of chemical and biological systems and changes occurring therein. For example the determination of the output of light from a sample containing luminescent microorganisms provides a highly sensitive technique for observing the effect of a substance on the metabolism of the microorganism. In carrying out such procedures it is important that the sample be disturbed as little as possible during the light measurement process in order to prevent undesirable fluctuation in the light signal from the sample. Likewise it is important, particularly when the sample involves living organisms, to control the sample temperature as light output can be highly temperature sensitive.

As is conventional in the art, the light output from a sample, be it light from an external light source passing through the sample or light generated from the sample itself, is directed from the sample to a photosensitive device which produces a signal responsive to the intensity of the light impinging thereon. The signal is passed by known circuitry to a readout device such as a meter or recorder. In order to provide efficient utilization of light, the sample and photosensitive device are mounted in close proximity to each other and to the light source, if one is required. Maximum compactness is obtained with instruments employing the so-called "Turret" design reaction chamber such as disclosed in U.S. Pat. No. 3,764,214 (Heiss). However such devices require movement of the sample during the opening and closing of the shutter in the operation of the instrument.

As already mentioned, many luminescent reactions, particularly bioluminescence, are highly temperature sensitive and temperature control of the sample during luminescence measuring operations is important for consistent, reproducible results. Conventional instrumentation, including Heiss, require that a large body mass of the instrument be cooled or heated if control of the sample temperature is desired.

SUMMARY OF THE INVENTION

The present invention relates to an improved sample-chamber and shutter assembly for use in combination with a photometer for the measurement of light emission, in which the sample can be maintained within a controlled temperature range. The mechanism is compact and has minimal thermal mass, thus readily permitting temperature control of the sample. Operation of the photometer shutter is carried out without moving or disturbing the sample.

More particularly the assembly comprises a stationary, thermally conductive body provided with a sample chamber mounted in close proximity to the photosensitive device of the photometer. A light path is provided for passage of light between the sample chamber and the photosensitive device. A shutter mechanism is mounted over the photosensitive device and is operative independently of any movement of the sample chamber between a closed position in which the passage of light to the photosensitive device is blocked and open position in which the photosensitive device is exposed to light emitting from the sample chamber. The sample chamber thermally communicates with a heat exchanger for the conduction of heat between the sample chamber and the heat exchanger to control the temperature in the sample chamber.

Other features of the invention reside in the provision of an external closure which rotates with the shutter to close the exterior opening of the sample chamber when the shutter is rotated to the open position; improved flexible heat conducting means for thermally connecting the stationary body and the heat exchanger, and means for purging the sample chamber with dry gas to prevent fogging of the sample container. It is within the scope of the invention to provide an external light source for use of the apparatus of the invention in colorimetric or spectrophotometric applications and for the measurement of fluorescence and scattered light.

These and other advantages and features of the invention will become apparent from the following description of the preferred embodiment taken in conjunction with the accompanying drawings, which illustrate by way of example the principles of the present invention.

DESCRIPTION OF THE PREFERRED EMBODIMENT

Figure 1:
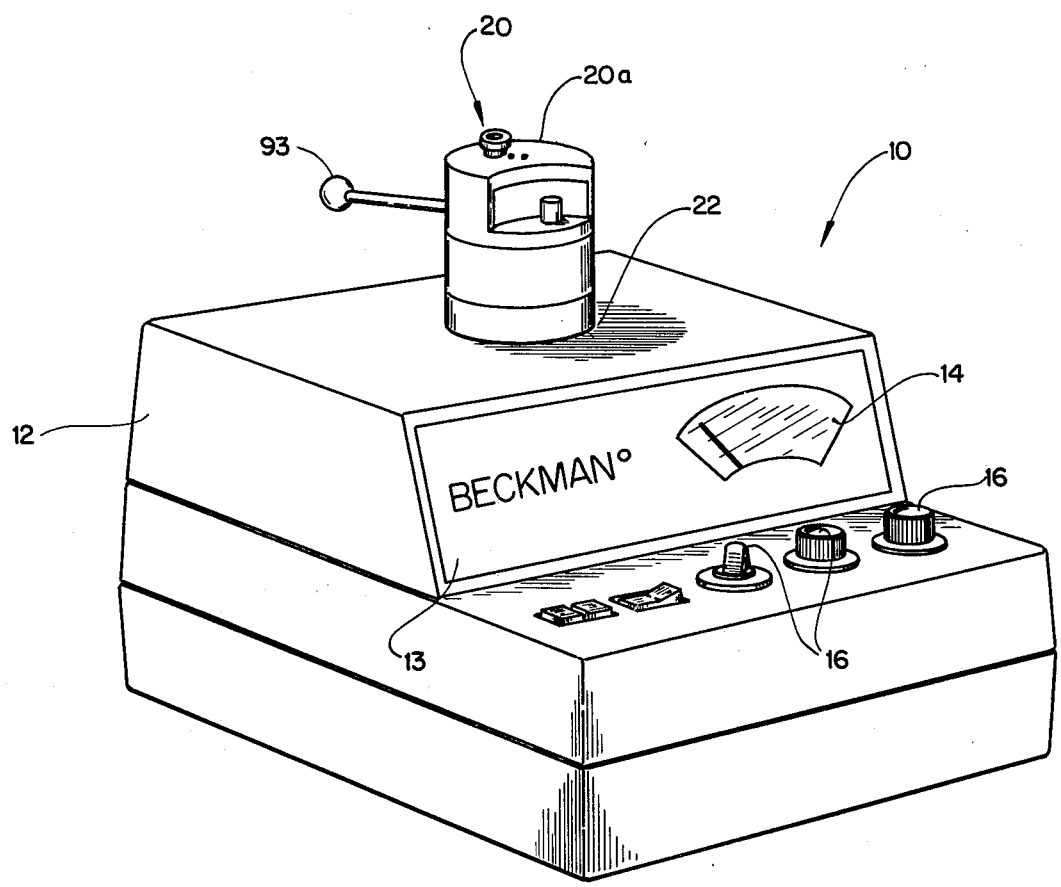
FIG. 1 is an isometric view of a photometer constructed in accordance with the invention.

Referring to the drawings wherein like reference characters refer to like parts throughout the several figures, a photometer, shown generally as 10, includes a main housing 12 having a front panel 13 in which is inset a readout meter 14 and control knobs 16. Conventional electrical circuitry, not illustrated, is employed in photometer 10. If desired the photometer 10 can be connected to a conventional recording or printout device, not shown, for permanent record of the output from the photometer. A photosensitive device, for example photomultiplier tube 18, is mounted in the main housing 12 and is connected electrically into the instrument circuitry by a socket and base assembly 19. As is well understood in the art, other photosensitive devices can be utilized such as for example, photodiodes, phototransistors, photoresistors and photo field effect transistors can be employed in the present invention.

Figure 2:
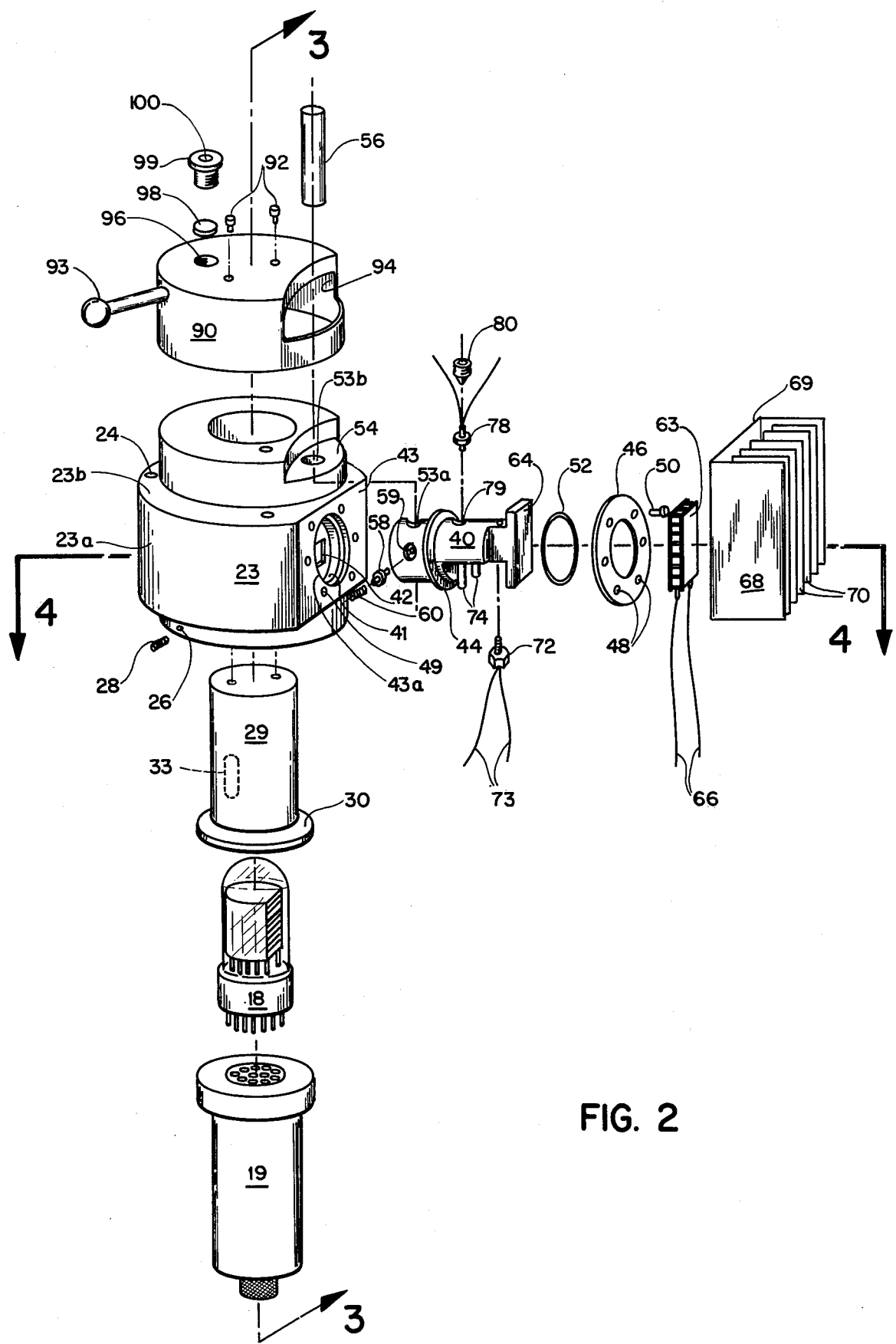
FIG. 2 is an exploded isometric view of a sample holder and shutter assembly constructed in accordance with the invention.
Figure 3:
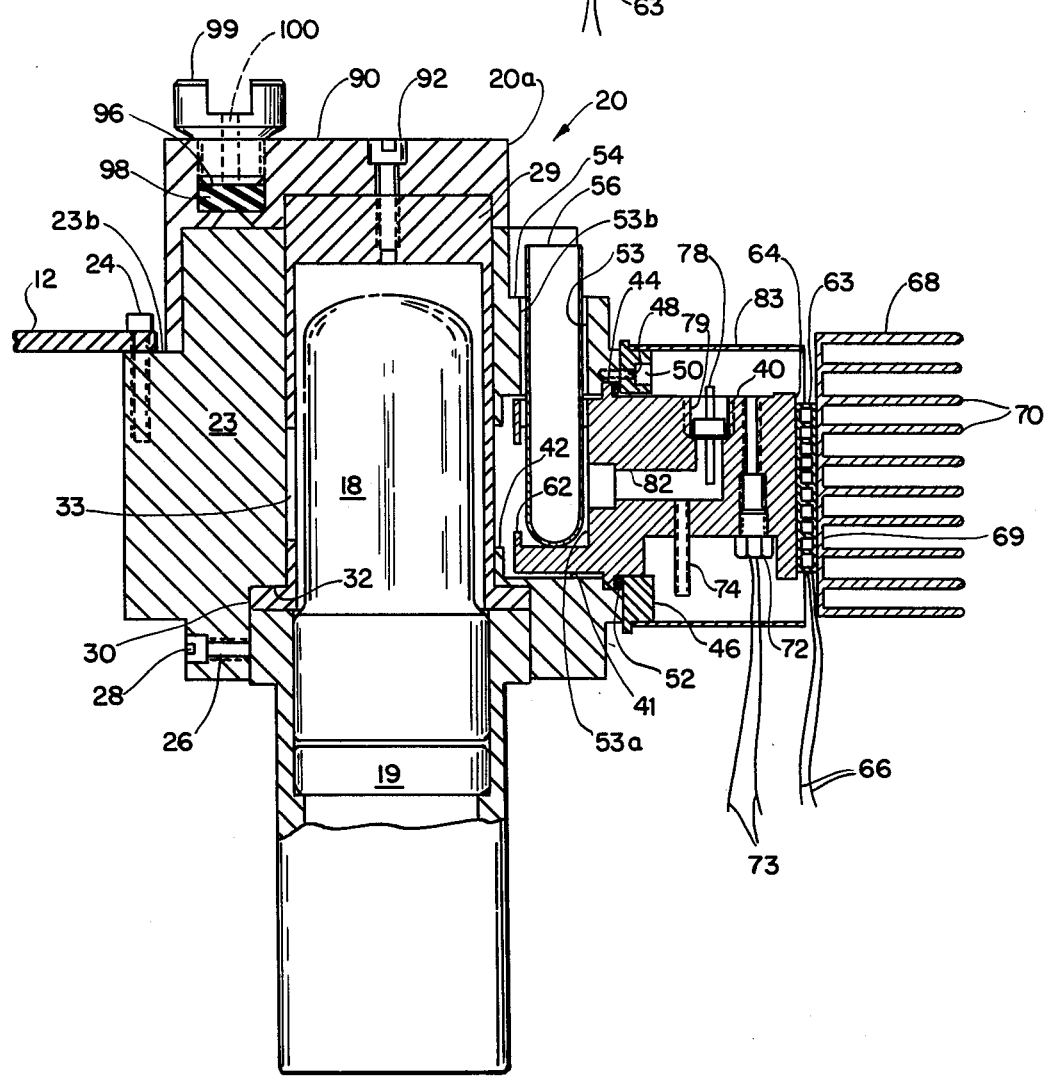
FIG. 3 is a sectional view in enlarged scale taken through line 3—3 of FIG. 2.

As is most clearly shown in FIGS. 1, 2 and 3, a sample chamber and shutter assembly, indicated generally as 20, constructed in accordance with the invention, is mounted in the photometer 10 in close proximity to the photomultiplier tube 18 and the upper portion 20a of the assembly extends exteriorly of the photometer through an opening 22 in the top wall of the main housing 12. More specifically, the sample chamber and shutter assembly includes a generally annularly shaped stationary turret body 23 having an enlarged diameter center portion 23a and a shoulder 23b extending around the periphery of the turret body. The turret body 23 is secured to the upper wall of the main housing 12 by suitable fastening means such as a bolt 24 threadably engaged in the turret body 23 at the shoulder 23b. The turret body 23 surrounds the photomultiplier tube 18 and the upper portion of the socket and base assembly 19. At least one threaded passage 26 extends through the wall of the turret body 23 and contains an adjustment screw 28 for clamping the socket and base assembly 19 and for adjusting alignment of the photomultiplier tube 18 with respect to the axis of the turret body.

A shutter housing 29, closed at one end, and having a radially outwardly extending flange 30 at its opposite open end encloses and contains the photomultiplier tube 18. The housing 29 is rotatably mounted on the upper face of the socket and base assembly 19 and the flange rides in a channel 32 defined by a recess lower portion of the inner wall of the turret body 23 and the upper edge of the socket and base assembly 19. The housing is provided with an aperture 33 which, upon rotation of the housing, can be aligned with the photosensitive element in the photomultiplier tube 18.

A sample chamber body 40 is mounted on one side of the turret body 23 by means of an exteriorly opening mounting cavity 41 which extends through a substantial portion of the wall of the turret body normal to the axis of the turret body. The exterior wall portion surrounding the opening of the mounting cavity 41 is machined to define a generally planar surface area 43 and a groove 43a around the opening of the mounting cavity 41. The wall portion of the turret body 23 defining the inner wall of the mounting cavity is provided with a port 42 for light communication between the cavity and the interior of the turret body. An end portion of the sample chamber body 40 is configured to the size and shape of the mounting cavity 41 and is received therein. A flange 44 on the sample chamber body 40 limits the insertion of the sample chamber body into the mounting cavity 42 and the flange is seated in the groove 43a and its under surface bears against the bottom surface of the groove when the sample chamber body is mounted in the turret body 23. A clamping ring 46 having an opening sized to fit around the sample chamber body 40 is provided with holes 48 which are aligned with threaded holes 49 and screws 50 to secure the clamping ring against the planar surface portion 43 of the turret body 23. An O-ring 52 is disposed between the clamping ring 46 and the flange 44 of the sample holder body 40.

A sample chamber 53 is defined by socket 53a in the end portion of the sample chamber body 40 and the socket is aligned with a passage 53b extending through the top wall of the turret body 23 opening to the exterior at a right angularly cut-away portion 54. The sample chamber 53 is dimensioned to receive a transparent cuvette 56. A flanged plunger 58 is disposed in a passage 59 which extends normal to the axis of the sample chamber and communicates therewith. The outer portion of the passage 59 is enlarged to receive the flange of the plunger 58 and a spring 60 which urges the plunger inwardly so that the inner plunger end contacts the cuvette when it is disposed in the sample chamber.

Communication between the sample chamber 53 and the interior of the turret body 23 is provided by an aperture 62 in the end wall of the sample chamber body adjacent the sample chamber and the port 42 in the adjacent wall of the turret body.

Temperature control within the sample chamber 53 is achieved by a thermoelectric heat pump 63 in intimate thermal contact with a heat transfer face 64 formed on the end of the sample holder body 40 opposite to the end received in the mounting cavity 41 of the turret body 23. The thermoelectric heat pump 63 operates according to the well known Peltier effect in which the polarity of an electrical current passed through the unit through leads 66 connected to a source of polarized current, not shown, determines whether the unit works to supply or remove heat from the sample chamber 53.

The sample chamber body 40 is formed from a material having a high coefficient of thermal conductivity for ready transfer of thermal energy between the heat pump and the sample chamber 53. Preferably the sample chamber body 40 is formed of material having a coefficient of thermal conductivity of 1.5 w/cm$^2$ °C./cm or greater.

Thermal communication between the sample chamber body 40 and the turret body 23 is maintained at a minimum, preferably by forming the turret body of a substantially thermally nonconductive material. In addition thermal insulation can be provided at the areas of contact between the sample chamber body 40 and the turret body 23 such as between the walls of the mounting cavity 41 and the end portion of the sample chamber body and at the contacting surfaces of the flange 44 and planar surface area 43 of the turret body.

The heat pump 63 is in intimate thermal contact with a heat reservoir 68, such as for example a plate 69 formed of thermally conductive material having a plurality of heat exchange fins 70 affixed in thermal contact on the side of the heat pump 63 opposite to the sample chamber body 40. A thermistor 72 is disposed in the sample chamber body 40 and is connected by leads 73 to a heat pump controller of conventional design, not shown, for controlling the flow of current to the heat pump 63. The thermistor 72 is located on the sample chamber body 40 near the heat pump 63 to reduce thermal response time.

Figure 4:
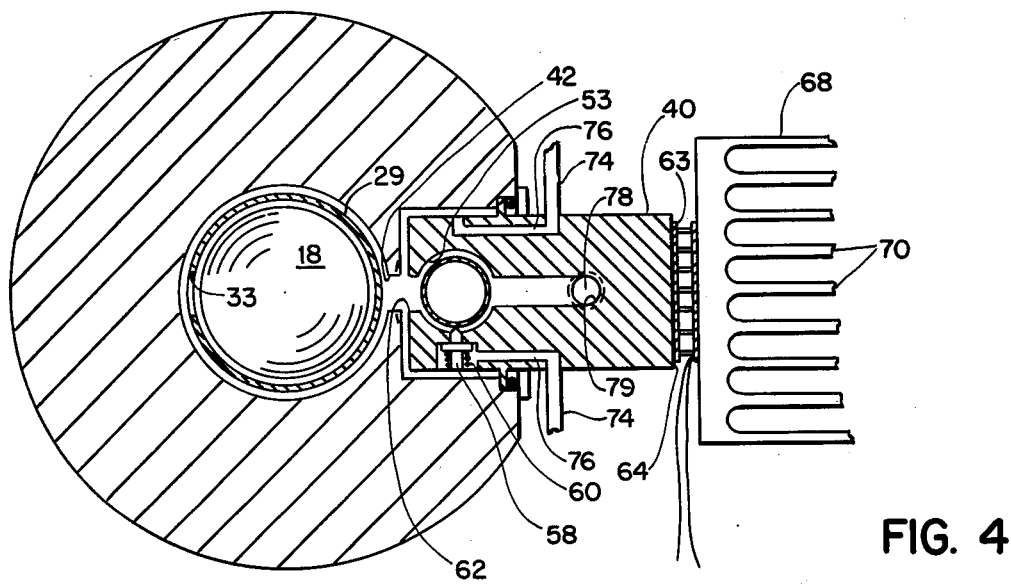
FIG. 4 is a sectional view in enlarged scale taken through line 4—4 of FIG. 2.
Figure 5:
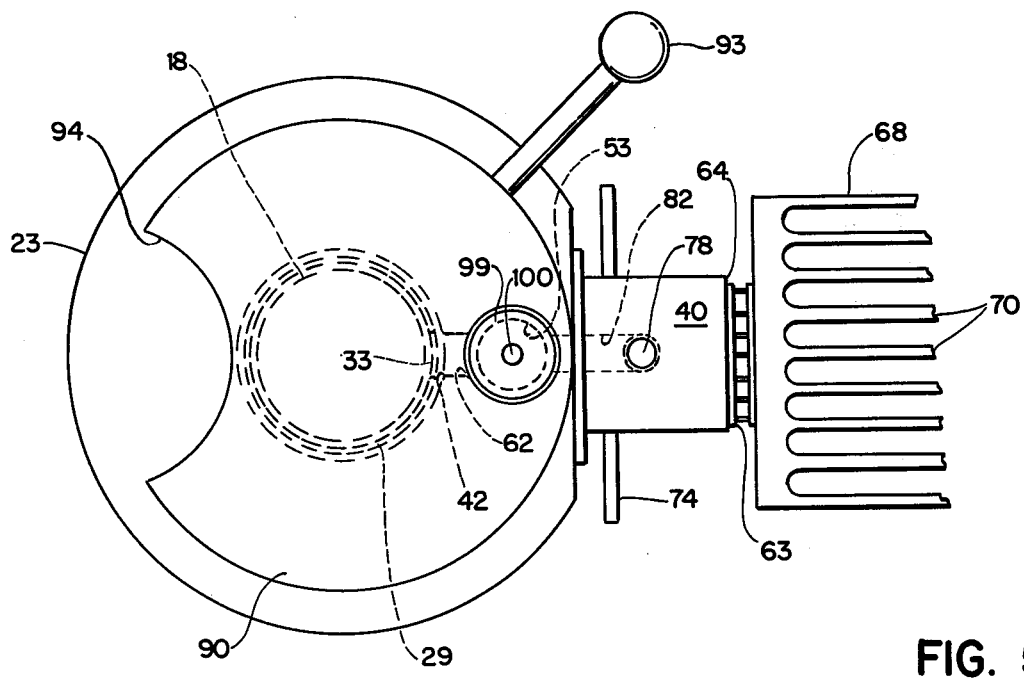
FIG. 5 is a top view of the sample holder and shutter assembly constructed in accordance with the invention.

The sample chamber body 40 is provided with tubes 74 for the circulation of a gas of controlled humidity through the sample chamber 53 by means of passages 76 (FIG. 4). The dry gas prevents fogging of the cuvette 56 during operation of the photometer 10.

A standard light output for test signal purposes is provided by a light emitting diode (LED) 78 which is received in a mounting socket 79 and held therein by suitable means, such as a hollow threaded bushing 80. Light output from the LED 78 passes through an axial bore 82 to the sample chamber 53.

A tubular housing 83 is disposed about the exposed portions of the sample chamber body 40 for insulation purposes. The space between the housing 83 and the body 40 can be filled with an insulating material.

The assembly 20 is completed by an inverted, cap-shaped outer rotary shutter 90, which fits over the upper portion of the turret body 23 to define the exterior of the upper portion 20a of the assembly. The outer shutter 90 is secured by suitable means, such as screws 92 to the inner shutter housing 29 and the outer shutter 90 carries an operating arm 93, the operation of which causes simultaneous rotation of the outer shutter and the inner shutter housing to expose the photomultiplier tube 18 to the sample chamber 53 without movement of the sample chamber. The outer shutter housing 90 is provided with an opening 94 to permit access to the sample chamber 53 when the opening is aligned over the sample chamber. The opening 94 is preferably of substantially matching dimensions as the cut-away portion 54 of the turret body 23 to permit ready access to the sample chamber 53. A second opening 96 is provided through the top of the outer shutter housing 90 and a septum 98 of suitable sealable material, such as rubber, is disposed in the opening to normally seal it. The septum 98 is penetrable to allow a syringe needle to pass therethrough and is self sealing when the needle is withdrawn. A septum clamp screw 99 having an axial needle guide bore 100 extending therethrough is threadably engaged in the opening 96 to retain the septum 98 in place. The second opening 96 is located on the outer rotary shutter 90 so that it is aligned over the sample chamber 53 when the inner shutter housing 29 is in the open position.

Operation of the photometer 10 is begun as illustrated in FIG. 4 with the inner shutter housing 29 in the closed position blocking the light path between the photomultiplier tube 18 and the sample chamber 53 by misalignment of the aperture 33 with the turret body port 42 and the sample chamber body aperture 62. The aperture 94 of the outer shutter 90 is substantially aligned with the cut-out portion 54 of the turret body 23 to expose the opening of the sample chamber 53.

For purposes of illustration it will be assumed that the temperature in the sample chamber 53 is to be maintained below ambient. For example in the case of bioluminescence, it is generally desirable to maintain the sample chamber 53 at a temperature below ambient, on the order of 15° C.–20° C. Accordingly, current is driven through the heat pump 63 so that, in accordance with the Peltier effect, the heat pump operates to remove heat from the sample chamber body 40 and sample chamber 53. A flow of dry gas is maintained in the sample chamber 53 by introducing the gas through one of the tubes 74 and corresponding passage 76 and exiting the gas through the other passage and tube. The cuvette 56 is inserted into the sample chamber 53 and held firmly by the inward pressure of the plunger 58 responsive to the urging of the spring 60. The contact between the cuvette and the wall of the chamber 53 due to plunger 58 aids in the transfer of heat from the cuvette contents through the cuvette wall to the sample chamber body 40.

The arm 93 is operated to simultaneously rotate the outer shutter 90 approximately 180° to completely cover the sample chamber 53 to prevent stray light from entering and to rotate the inner shutter housing 29 into the open position with the aperture 33 aligned with the light path defined by the port 42 and aperture 62 to expose the photomultiplier tube to light emission from the sample chamber 53. The sample chamber 53 and sample remain stationary during the opening of the shutter housing 29. The dry gas is circulated during operation of the assembly 20 to avoid fogging of the cuvette which could occur if the dew point of the atmosphere in the sample chamber 53 were exceeded due to cooling of the sample chamber and cuvette.

The output of the photomultiplier tube 18 due to the impingement of light thereon is noted or recorded while the inner shutter housing 29 is in the open positon.

It should be noted that the contents of the sample can be introduced into the cuvette 56 prior to its introduction into the sample chamber 53 and since the sample chamber is not moved during operation of the photometer 10, reaction rates and light output are unaffected by rotation of the shutter housing 29 and outer shutter 90. In addition, however, one or more components of the sample can be introduced while the shutter housing 29 is in the open position by a hypodermic needle through the needle guide bore 100 of the septum clamp screw 99 and septum 98 which are aligned over the sample chamber 53 when the shutter housing is in the open position. This method is particularly useful in reaction rate measurements or when determining rapid rate changes in metabolic functions of microorganisms and the like.

The design and operation of the assembly 20 and the stationary sample chamber also permits the use of stirring means such as a magnetic stirrer or the like in the cuvette. Such stirring means are particularly useful for certain colorimetric and reaction rate studies where the sample requires continuous stirring during the measurement of light output.

Testing and balancing of the components of the photometer 10 is accomplished from time to time by generating a standard light output from the LED 78 while the photomultiplier 18 is open to the sample chamber 53. A cuvette containing a blank, such as demineralized water, may be located in the sample chamber 53 for calibration purposes.

In the embodiment of the invention shown in FIGS. 2, 3, 4 and 5 the heat reservoir 68 is a separate unit attached directly to the heat pump 63. Heat exchange is between the fins 70 of the heat reservoir 68 and the atmosphere in the main housing 12. Such a design necessitates a rigid connection between the heat pump 63 and the heat reservoir 68. The thermoelectric unit utilized as the heat pump 63 is fragile and the rigid connection of the heat sink to the heat pump can result in undue stress and ultimate failure of the thermoelectric unit. In addition from the standpoint of economics, the heat reservoir 68 must have a relatively large surface area in order to achieve the desired heat exchange capacity.

In accordance with the invention there is provided an improved design for the transfer of heat between the heat pump and the main housing, which acts as the heat reservoir. The heat transfer means is flexible thus removing the stresses on the fragile heat pump imposed by a rigid attachment to the heat sink.

Figure 6:
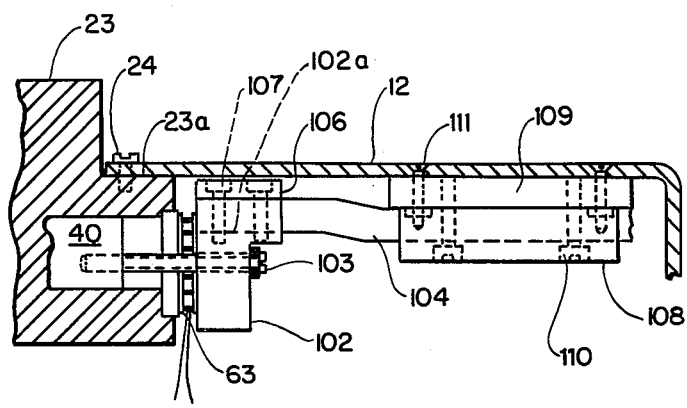
FIG. 6 is a side sectional view of a portion of a photometer illustrating an embodiment of the invention where the sample holder and shutter assembly is connected by flexible means for heat transfer between the housing and the assembly.

As is shown in FIG. 6, the turret body is secured to the main housing 12 by bolts 24 at its shoulder 23b. The sample chamber body 40 is mounted on the turret body 23, and carries the heat pump 63 as already described. One face of the heat pump 63 is in intimate thermal contact with the sample chamber body 40 and the opposite face is secured in intimate thermal contact with a thermal termination block 102 by means of clamp screws 103 which extend through the block and are threadably engaged in the sample chamber body on each side thereof. The termination block 102 includes a channel 102a in which is received one end of a flexible, thermally conductive, solid member 104 which is secured therein by a clamping bar 106 and screws 107. The flexible thermally conductive member 104 may be formed of any conductive flexible material such as metal filled plastic or soft aluminum, brass or copper strip. Good results, i.e. high thermal conductivity and flexibility, are achieved using one or more layers of braided copper wire. The opposite end of the conductive member 104 is received in a channel provided in a U-shaped terminal 108 which is secured to a plate 109 by bolts 110. The plate is secured to the under surface of the top portion of the main housing 12 by screws 111. When using braided conductive wire as the conductive member 104, the terminal end portions can be impregnated with a conductive filler material, such as silver filled epoxy, to fill voids in the braid and improve thermal transfer through the terminal end portions.

As illustrated, the flexible conductive member 104 is bent or flexed slightly after assembly. This provides a degree of slack in the conductive member 104 and permits relative movement of the block 102 and terminator 108 with respect to each other without stressing or straining the conductive member or the heat pump 63.

From the foregoing it will be appreciated that the sample holder and shutter assembly of the invention provides a sample chamber in which the temperature is controlled yet which is compact and in close proximity to the photosensitive device. The invention is particularly suitable for use in the determination of light from luminescent sources such as suspensions of bioluminescent organisms. The design permits little or no stray light leakage and provides protection for the photosensitive device even when the sample chamber is exposed. In addition to the foregoing, the device of the present invention is operable without moving the sample chamber which facilitates reproducible and accurate determination of light intensity from samples which are sensitive to movement, particularly luminescent microorganisms and also permits the addition of ancillary features such as dry gas purging of the sample chamber and continuous stirring features with a minimum of design change and expense.

While a particular form of the invention has been illustrated and described, it will be apparent that various modifications can be made without departing from the spirit and scope of the invention.

What is claimed is:

1. A sample holder and shutter assembly for use in instruments mounting a photosensitive device for the determination of light, said assembly comprising:
    a stationary body having a sample chamber, and a light path opening from said sample chamber to the photosensitive device;
    means for mounting said stationary body in relation to the photosensitive device for the detection of light transmitted from said sample chamber;
    shutter means comprising an opaque housing containing the photosensitive device and shielding the photosensitive device from light transmitted from said sample chamber when in the closed position, said housing having an aperture for communication between said photosensitive device and said light path from said sample chamber when said shutter means is in an open position to expose the photosensitive device to light transmitted therefrom;
    heat exchange means for controlling the temperature in said sample chamber; and
    means for closing said sample chamber to external stray light when said shutter means is in the open position.

2. The assembly of claim 1 wherein said heat exchange means comprises a thermoelectric unit having a first thermal connection with said stationary body and a second thermal connection with a heat reservoir, and means for passing polarized current through said thermoelectric unit, said thermoelectric unit being operable according to the Peltier effect to transfer heat between said body and said heat reservoir responsive to the polarity of the current passing therethrough.

3. The assembly of claim 1 wherein said stationary body has a coefficient of thermal conductivity sufficient to permit the passage of thermal energy between said sample chamber and said heat exchange means and is out of thermal communication with said mounting means.

4. The assembly of claim 1 wherein said stationary body further includes means for directing a circulating flow of a gas of selected humidity through said sample chamber.

5. The assembly of claim 1 wherein said means for mounting said stationary body comprises a stationary turret body having a central bore for receiving the photosensitive device and said shutter means, a mounting cavity extending normal to said bore from the exterior of said turret body for receiving a portion of said stationary body and means for securing said stationary body in said mounting cavity, said mounting cavity having a port for light communication with the bore of said turret body and a passage opening at the upper surface of said turret body being in aligned communication with said sample chamber when said stationary body is mounted on said turret body.

6. The assembly of claim 1 wherein said heat exchange means comprises a heat pump in thermal contact with said stationary body and a heat reservoir for the transfer of thermal energy between said stationary body and said heat reservoir.

7. The assembly of claim 1 wherein said means for closing said sample chamber is operable with said shutter means so that when said shutter means is in the open position said sample chamber is closed to external stray light.

8. The apparatus of claim 1 further including a light source for projecting light into a sample in said sample chamber.

9. A photometric instrument comprising:
    means providing an instrument housing;
    photodetection means including a photosensitive device in said housing for providing an electrical signal responsive to the impingement of light thereon;
    a stationary body mounted on said housing, said body having an interior communicating with the interior of said housing means for receiving at least a portion of said photosensitive device, an exteriorly opening sample chamber for receiving and retaining a light transmitting sample container and a light path communicating between said body interior and said sample chamber;
    inner shutter means comprising a rotatable opaque housing surrounding said photosensitive device, said opaque housing shielding said photosensitive device from light when in the closed position and having an opening in one wall which upon rotation of said housing to an open position is brought into alignment with said light path to permit communication between said sample chamber and said photosensitive device;
    outer shutter means comprising an opaque cap rotatably mounted over the upper end of said stationary body, said cap normally providing a light tight closure over said exteriorly opening sample chamber and having an opening for alignment with said sample chamber for access thereto upon rotation of said cap;

means for the rotation of said inner shutter means and said outer shutter means to close said exteriorly opening sample chamber to external stray light when said inner shutter means is in the open position; and heat exchange means thermally connected with said stationary body for controlling the temperature of said sample chamber.

10. The apparatus of claim 9 wherein said stationary body is thermally conductive and is thermally connected to a heat reservoir by a thermoelectric heat pump for the transfer of thermal energy therebetween.

* * * * *